United States Patent [19]

Rane et al.

[11] Patent Number: 4,731,364
[45] Date of Patent: Mar. 15, 1988

[54] DIHYDROBENZO(B)THIOPHENES AND PHARMACEUTICAL COMPOSITIONS THEREOF USEFUL AS ANTIFUNGALS

[75] Inventors: Dinanath F. Rane, Sayreville; Russell E. Pike, Stanhope, both of N.J.

[73] Assignee: Schering Corporation, Kenilworth, N.J.

[21] Appl. No.: 764,289

[22] Filed: Aug. 12, 1985

[51] Int. Cl.$^4$ .................... A01N 43/84; C07D 409/06
[52] U.S. Cl. .................... 514/222; 514/231; 514/253; 514/254; 514/324; 514/337; 514/361; 514/383; 514/397; 544/58.5; 544/62; 544/132; 544/139; 544/366; 544/370; 546/202; 546/274; 548/127; 548/262; 548/269; 548/336
[58] Field of Search ............... 548/336, 262, 269, 127; 544/139, 132, 370, 366, 58.5, 62; 514/397, 383, 231, 253, 254, 324, 361, 222, 337; 546/202, 274

[56] References Cited

U.S. PATENT DOCUMENTS 4,352,808 10/1982 Rane et al. .................. 548/336 X
4,431,816 2/1984 Rane et al. .................. 548/336
4,496,572 1/1985 Cross et al. .................. 548/336 X

FOREIGN PATENT DOCUMENTS 54233 6/1982 European Pat. Off. .......... 548/336
644855 8/1984 Switzerland .................. 549/451

OTHER PUBLICATIONS

C. Djerassi, *Steroid Reactions,* Holden-Day Inc., 1963, San Francisco, pp. 1–66.
I. T. Harrison, et al., *Compendium of Organic Synthetic Methods,* Wiley-InterScience, New York, 1971, pp. 449–456.

*Primary Examiner*—Richard A. Schwartz
*Attorney, Agent, or Firm*—Thomas D. Hoffman; Gerald S. Rosen

[57] ABSTRACT

2-Alkyl-, 2-alkenyl- and 2-alkynyl-2,3-dihydro-2-(1H-azolyl($C_1$-$C_2$)alkyl)benzo[b]thiophenes especially 2-alkyl-, 2-alkenyl- and 2-alkynyl-2,3-dihydro-3-hydroxy-2-(1H-1-imidazolylmethyl)-4-,5-,6- and 7-halobenzo[b]-thiophenes and related derivatives having antifungal activity are disclosed. Pharmaceutical compositions comprising compounds of the invention and their use in treating fungal infections in susceptible hosts such as humans are also disclosed.

21 Claims, No Drawings

DIHYDROBENZO(B)THIOPHENES AND PHARMACEUTICAL COMPOSITIONS THEREOF USEFUL AS ANTIFUNGALS

BACKGROUND OF THE INVENTION

This invention relates to 2-alkyl-, 2-alkenyl and 2-alkynyl-2,3-dihydro-2-[1H-azolyl($C_1$-$C_2$)alkyl]-benzo[b]thiophenes and related derivatives which exhibit antifungal activity, pharmaceutical compositions thereof and methods for their use in treating fungal infections in a host including warm-blooded animals such as humans.

Various antifungal 2,3-dihydro-2-(1H-1-imidazolyl-methyl)benzo[b]thiophenes are known. For example U.S. Pat. No. 4,431,816 discloses 3-hydroxy-2,3-dihydro-2-(1H-1-imidazolylmethyl)benzo[b]thiophenes and European patent application No. EP 54,233 discloses cis-6-chloro-3-allyloxy-2,3-dihydro-2-(1H-1-imidazolylmethyl)-benzo[b]thiophene.

However, none of the references are directed to the 2-alkyl, 2-alkenyl or 2-alkynyl the compounds of this invention.

SUMMARY OF THE INVENTION

The compounds of this invention are represented by the following formula I:

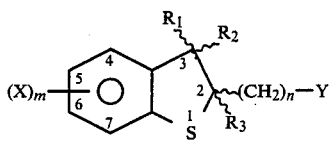

in racemic or optically active form, or a pharmaceutically acceptable salt thereof wherein X is one or more groups selected independently from halogen, (lower)alkyl, halo(lower)alkyl, cyano, nitro and phenyl and phenyl(lower)alkyl;

Y is substituted or unsubstituted imidazolyl or 1,2,4-triazolyl, said substituents being one or more groups selected independently from (lower) alkyl or phenyl and phenyl(lower)alkyl;

$R_1$ and $R_2$ are independently hydrogen, —$CH_2NR_4R_5$, —$NR_4R_5$, —$OR_4$, —$SR_5$, (lower)alkyl, (lower) alkenyl, phenyl and phenyl(lower)alkyl, halogen, substituted or unsubstituted phenyl and phenyl (lower)alkyl, and phenyl and phenyl(lower)alkyl substituted by one to four of one or more groups selected from halogen, nitro, —$NR_4R_5$, (lower)alkanoyl. (lower)alkyl or halo(lower)alkyl or $R_1$ and $R_2$ taken together with the carbon in the 3 position form carbonyl, thiocarbonyl, >C=N—$R_4$,

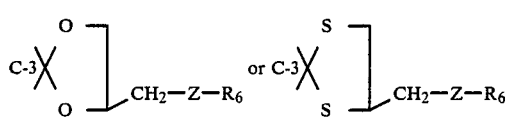

$R_3$ is —CH—C≡$CR_8$ or —CH—C=$CHR_8$ or
           |                    |    |
           $R_7$                $R_7$  $R_9$

—CH—CH—$CH_2R_8$;
  |    |
  $R_7$  $R_9$ and $R_6$, $R_7$, $R_8$ and $R_9$ are independently hydrogen, (lower) alkyl, substituted or unsubstituted phenyl and phenyl(lower)alkyl, said phenyl and phenyl(lower)alkyl substituents being as described hereinabove, or substituted or unsubstituted heterocyclyl, said heterocyclyl substituents being halogen, (lower)alkyl, (lower)alkanoyl, or subsittuted or unsubstituted phenyl and phenyl(lower)alkyl;

$R_4$ and $R_5$ are independently hydrogen, (lower)alkyl, (lower)alkenyl, N,N-di(lower)alkyl carbamoyl, N,N-di(lower)alkyl thiocarbamoyl, arylcarbonyl, substituted or unsubstituted phenyl and phenyl(lower)alkyl, said phenyl and phenyl(lower)alkyl substituents being as described hereinabove, or $R_4$ and $R_5$ taken together with the nitrogen atom in —$NR_4R_5$ and —$CH_2NR_4R_5$ form substituted or unsubstituted heterocyclyl;

Z is O, S or $NR_5$;

m is 1, 2, 3 or 4; and n is 1 or 2.

This invention also provides a pharmaceutical composition comprising an antifungally effective amount of a compound represented by formula I or a pharmaceutically acceptable acid salt thereof, together with a pharmaceutically acceptable carrier or diluent.

This invention further provides a method of treating susceptible fungal infections which comprises administering to a host, e.g., warm-blooded animals including humans, in need of such treatment an antifungally effective amount of a compound represented by formula I or a pharmaceutical composition comprising such a compound and a pharmaceutically acceptable carrier or diluent.

In particular, this invention relates to 2-alkyl-2-alkenyl-and 2-alkynyl-dihydro-2,3-dihrydro-3-hydroxy-2-(1H-1-imidazolylmethyl)-4-,5-, -6-, and -7-halobenzo[b]-thiophenes, pharmaceutical compositions comprising them and methods of using said pharmaceutical compositions to treat susceptible fungal infections in a host, e.g., warm-blooded animals, in need of such treatment.

DETAILED DESCRIPTION OF THE INVENTION AND THE PREFERRED EMBODIMENTS

As used in the specification and claims, the term "halogen" means bromine, chlorine or fluorine with chlorine and fluorine being preferred; fluorine is more preferred. The term "(lower)alkyl" refers to straight and branched chain hydrocarbon groups of 1 to 6 carbon atoms, such as methyl, ethyl, n-, and iso-propyl, n-, sec- and tert-butyl, n-, sec-, iso-, tert- and neo-pentyl, n-, sec-, iso-and tert-hexyl. The term "halo(lower)alkyl" refers to "(lower)alkyl" groups having at least one halogen substitutent, e.g., —$CH_2$—$CF_3$, —$CF_2$—$CH_3$ as well as per halo groups such as —$CF_2$—$CF_3$ OR—$CE_3$; trifluoromethyl is preferred. The term "(lower)alkanoyl" refers to straight and branched chain alkanoyl groups having 2 to 8 carbon atoms such as acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 2-methylheptanoyl, octanoyl, 2-ethylhexanoyl and the like. Acetyl is preferred.

The term "heterocyclyl" refers to five and six-membered ring systems containing carbon and one to four heteroatons chosen from N, O and S. Typical suitable heterocyclyls include morpholino, piperazino, pyrrolidino, piperidino, imidazolyl, 1,2,4-triazolyl, furanyl, thienyl, thiadiazolyls (especially 1,2,3-thiadiazol-4-yl, and 1,2,3-thiadiazol-5-yl), thiomorpholino, and pyridyls. The heterocyclyl may be attached via a carbon atom, e.g., N-methylpiperidin-4-yl, N-methylmorpholin-2-yl or via the nitrogen atom, e.g., piperidin-1-yl (commonly called piperidino), morpholin-4-yl (commonly called morpholino),N-methylpiperazin-4-yl (commonly called N-methylpiperazino), 1H-1-imidazol-1-yl or 4 H-1,2,4-triazo4-yl. Azolyls, especially 1H-1-imidazolyl and 1H-1,2,4-triazolyl and pyridyls, especially 2-pyridyl and 2-or 3-thienyls are the preferred heterocyclyls.

Substituted heterocyclyls include (lower)alkyl heterocyclyls especially N-(lower)alkylheterocyclyls such as N-methylmorpholin-4-yl, N-ethylpiperazino, but also 2-methylpyrrolidino, 4-methylpiperidino, 5-methyl-1H-1,2,4-triazol-3-yl, 3-methyl-1-phenyl-1H-1,2,4-triazol-5-yl, and 2-methylpyridyl; (lower)alkanoyl heterocyclyls such as 2-acetylthiophenyl, 2-acetylpyrrolidino; halohetero-cyclys such as 2-halo-3-thienyl, 2,5-dihalo-3-thieny, and 5-halo-2-thienyl; N-(lower)alkanoyl heterocyclyls such as N-acetylpiperazino and 4-acetylpiperidino; and aryl substituted heterocyclyls include heterocyclyls substituted by aryl s defined herein such as N-phenylpiperazino, N-(4-chlorophenyl)piperazino, 2-(4-trifluoromethylphenyl)-piperazino, and the like. Azolyls, thiadiazolyls, thienyls, and pyridyls are the preferred substituted heterocyclyls.

By the term "(lower)alkenyl" as used herein is meant straight and branched chain alkenyl radicals of 2 to 8 carbon atoms such as vinyl, 1-and 3-propenyl, 1-butenyl, (cis)-and (trans-)-2-butenyl, 3-butenyl, 2-methyl-1-propenyl, 1-pentenyl, (cis)-and (trans)-2-and -3-pentenyl and 4-pentenyl, 1-, 2-, 3-, 4- and 5-hexenyl, 4,4-dimethyl-2-butenyl, 3,4-dimethyl1-butenyl, 1-heptenyl, 1-octenyl and the like.

The term "aryl" refers to phenyl, phenylalkyl and, phenyl and phenylalkyl substituted by one to four of one or more groups selected from halogen, nitro,—NR$_4$R$_5$ (with R$_4$ and R$_5$ being defined as hereinabove), (lower)alkanoyl, (lower)alkyl or halo(lower)alkyl. The term "phenylalkyl" refers to phenyl(lower)alkyl, especially benzyl, α- and β-phenylethyl and α-,β- and γ- phenylpropyl. The preferred phenylalkyl is benzyl. Typical suitable aryl groups include phenyl, halo substituted phenyl such as 4-chlorophenyl or 4-fluorophenyl, 2,4-dichloro- or 2,4-difluorophenyl, 2,5-dichloro-or 2,5-difluorophenyl, 2,6-dichloro- or 2,6-difluorophenyl, 2,4,6-trichloro-or 2,4,6-trifluorophenyl and 2,3,4,6-tetrachloro- and 2,3,4,6-tetrafluorophenyl; (lower)alkanoyl substituted phenyl such as 4-acetylphenyl; phenyl substituted by —NR$_4$R$_5$ such as 4-(N,N-dimethylamino)phenyl; phenyl substituted by two different groups such as 4-nitro-3-triflouromethylphenyl or 3-nitro-4-trifluoromethylphenyl; (lower)alkyl substituted phenyl such as 4-methylphenyl, 2,4-dimethylphenyl, 2,4,6-trimethylphenyl or 2,3,4,6-tetramethylphenyl; halo(lower)alkyl substituted phenyl such as 4-trifluoromethylphenyl, 4-(1,1-difluoroethyl)phenyl and similarly substituted phenylalkyl groups, especially similarly substituted benzyl groups. Difluoro and trifluophenyl are preferred aryl groups; 2,6-difluorophenyl is more preferred.

The term "arylcarbonyl" refers to "aryl" as defined hereinabove bonded to a carbonyl group and includes unsubstituted benzoyl and substituted benzoyl for example, 2,4-dichloro- and 2,6-difluorobenzoyl.

Preferred OR$_4$ groups include benzoyloxy, benzyloxy, substituted benzoyloxyl and substituted benzyloxy, said benzoyloxy and benzyloxy substituents being one to four of one or more groups selected from halogen, (lower)alkyl, halo(lower)alkyl, nitro, —NR$_5$R$_6$ or (lower)alkanoyl and 2-or 5-halo-3-thienyl, 3-halo-2-thienyl or 2,5-dihalo-3-thienyl.

Typical suitable substituted benzyloxy groups include 4-chlorobenzyloxy, 4-fluorobenzyloxy, 2,4-dichloro- or 2,4-difluorobenzyloxy, 2-chloro-4-fluoro-benzyloxy, 2,3-dichloro-or 2,3-difluorobenzyloxy, 2-chloro-3-fluorobenzyloxy, 2,5-dichloro-or 2,5-difluoro-benzyloxy, 2-chloro-5-fluorobenzyloxy, 2,6-dichloro- or 2,6-difluorobenzyloxy, 2-chloro-6-fluorobenzyloxy, 2-, 3-or 4-trifluoromethylbenzyloxy, 2-, 3- or 4-methyl-benzyloxy, 2-, 3- or 4-acetylbenzyloxy. Halobenzyloxy groups are preferred; 2,6-difluorobenzyloxy and 2,4-difluorobenzyloxy are particularly preferred.

Suitable compounds of formula I include (±)-cis- and -trans-isomers of:

(a) 2-allyl-6-chloro-2,3-dihydro-3-hydroxy-2-(1H-1-imidazolylmethyl)benzo[b]thiophene;

(b) 2-allyl-6-chloro-3-(2-chloro-6-fluorobenzyloxy)-2,3-dihydro-2-(1H-1-imidazolylmethyl)benzo [b]thiophene;

(c) 2-allyl-6-chloro-2,3-dihydro-3-fluoro-2-(1H-1-imidazolylmethyl) benzo [b]thiophene;

(d) 2-allyl-3-(2-chloro-6-fluorobenzyloxy)-2,3-dihydro-6-fluoro-2-(1H1-imidazolylmethyl)benzo[b]thiophene;

(e) 2-allyl-3-(2,6-difluorobenzyloxyl)-2,3-dihydro-6-fluoro-2-(1H-1-imidazolylmethyl)benzo[b]thiophene; and (f) 2-allyl-2,3-dihydro-6-chloro-2-(1H-1-imidazolylmethyl)benzo[b]thiophene.

Compounds of the present invention can exist in two isomeric forms, i.e., cis- 2,3 and trans- 2,3. For example (±)-2-allyl-6-chloro-2,3,-dihydro-3-hydroxyl-2-(1H-1-imidazolylmethyl)benzo[b]thiophene exists in the cis- and trans-forms as indicated by the following formulas

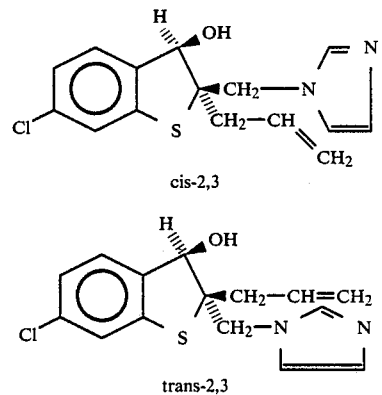

In the formula labelled cis, the hydroxy and 1H-imidazolylmethyl groups are both positioned on the same face of the formula. In the trans formula, the groups are positioned on opposite faces of the formula. Both forms are within the scope of the present invention, as are the individual optical isomers, i.e., e.g., (+)-cis-2,3 and (−)-cis-2,3 which can be obtained by resolution of a racemic mixture [(±)-cis-2,3] by conventional means well known to those skilled in the art.

The compounds of the present invention may be prepared by reacting substituted hydroxy compounds of the formula II wherein X, Y, m and n have the meanings given above with an allyl compound of the formula III, i.e., e.g., allyl-LG wherein LG is a leaving group such as halide, e.g., bromide, tosylate, mesylate and wherein $R_7$, $R_8$ and $R_9$ are as defined above, in the presence of an alkali metal base (MOH), a solvent or mixture of solvents for a time and temperature sufficient to give the substituted allyl ether of general formula IV, as depicted in the following reaction scheme.

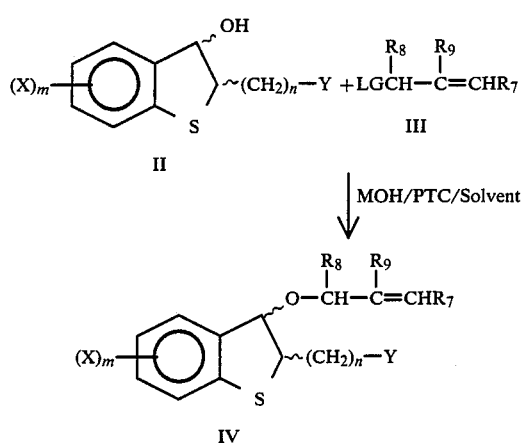

Compounds of formula II are prepared in accordance with the procedures disclosed in U.S. Pat. No 4,352,808 at Col. 5, lines 13–43 and at Col. 11 line 1 to Col. 12 line 9 (Preparation No. 1) which are hereby incorporated herein by reference.

The reaction of the compounds of formula II with an alkali metal base, i.e., for example an alkali metal hydroxide especially NaOH or KOH or aqueous solutions thereof, alkali metal hydride, alkali metal amide or alkali metal alcoholate and an allyl compound of formula III, e.g., allyl bromide is carried out in an aprotic organic solvent such as dimethylformamide, (DMF), dimethyl sulfoxide (DMSO), hexamethylphosphoric acid triamide (HMPTA), an ether such as tetrahydrofuran (THF), dioxane or dimethoxyethane, a lower alcohol, or a ketone, e.g., acetone and in the presence of a phase transfer catalyst (PTC) such as tricaprylylmethylammonium chloride at 0°–60° C., especially 20°–40° C. for 1–6 hours.

Compounds of formula IV are oxidized to give the substituted sulfoxide of formula V.

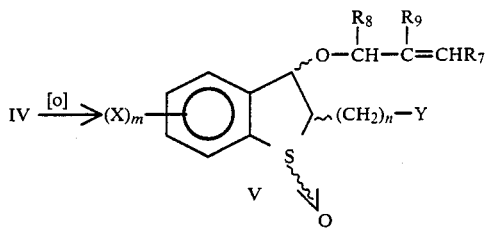

The oxidation of IV is typically carried out by contacting compounds of formula IV with an oxidizing agent such as a peracid e.g., meta-chloroperbenzoic acid or peracetic acid, or hydrogen peroxide in an organic solvent such as halogenated alkanes, e.g., methylene chloride or chloroform at about 0°–20° C., preferably 0°–5° C. 1–4 hours.

The substituted compounds of formula V are heated in a suitable solvent, and normally in the presence of an alkanoic acid anhydride, for a time sufficient to give the substituted ketone compounds of formula Ia.

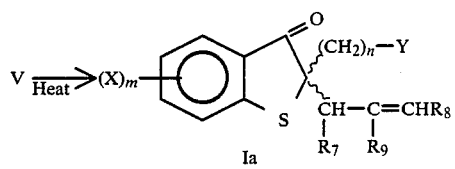

Typical suitable solvents include aromatic hydrocarbons such as benzene, xylenes, toluene, and halogenated alkanes such as chloroform.

Typical suitable alkanoic acid anhydrides include acetic anhydride, perchloroacetic anhydride and perfluoroacetic acid anhydride. Temperatures of about 50° to about 100° C. for about 1 to 2 hours are normally sufficient.

Compounds of formula I wherein $R_1$ and $R_2$ taken together with the carbon in the 3 position are thiocarbonyl, $>C=N-R_4$,

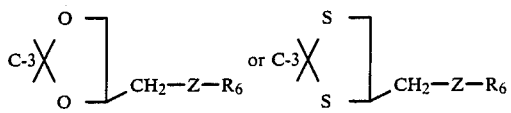

wherein Z, $R_4$ and $R_6$ are defined as hereinabove may be prepared from the substituted ketone compounds of formula Ia using standard chemical reagents such as disclosed in "Compendium of Organic Synthetic Methods" by I. T. Harrison and S. Harrison, Wiley-Interscience, pages 449–456 NY 1971 and "Steroid Reactions", C. Djerassi, Ed. Holden-Day Inc., pages 1–66 1963. For example, the ketals and thioketals of formula Ib may be prepared by an exchange reaction of Ia with dioxolans and dithioxolans of formulas VIa and VIb, respectively,

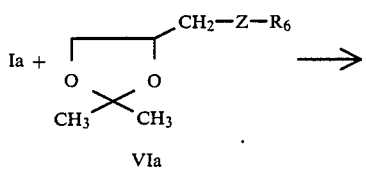

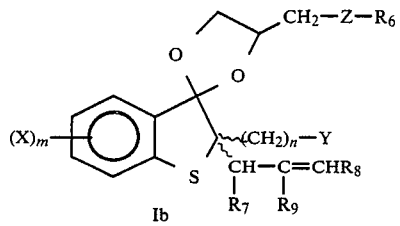

in the presence of acids such as toluenesulfonic acid (TsOH) in a solvent such as methylene chloride.

Typical dioxolans of formula VIa wherein Z=NH may be prepared by reductive amination of 2,2,dimethyl-4-formyl-1,3 dioxolans of the formula VII which are disclosed in Swiss patent Appln. No. CH644,855A (8/31/84).

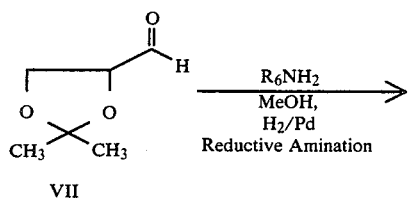

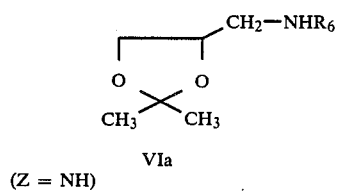

Compounds of formula Ic wherein $R_1$ and $R_2$ together with the carbon in the 3 position form $>C=NR_6$ may be prepared by reaction of compounds Ia with $R_6NH_2$, (normally as the acid addition salts) in the presence of a base such as sodium carbonate. The Schiff bases of formula Ic are purified by conventional techniques.

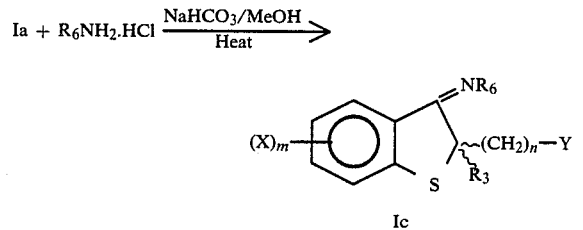

Thiocarbonyls of formula Id may be prepared by reaction of Ia with, for example, $P_2S_5$.

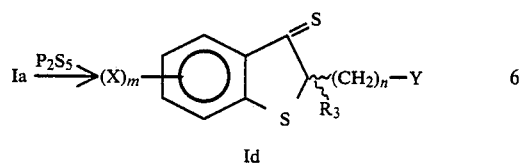

The compounds of formula I wherein $R_1$ and $R_2$ are hydrogen and hydroxyl are formed by reduction of compounds of formula Ia with metal hydride reagents, e.g., alkali metal borohydrides, especially $NaBH_4$ in lower alkanols, e.g., methanol, or with lithium aluminum hydrides such as $LiAlH_4$.

Compounds of this invention wherein $R_1$ and $R_2$ are hydrogen and $OR_4$ wherein $R_5$ is benzyl or substituted benzyl or arylcarbonyl, such as benzoyloxy or substituted benzoyloxy (said benzyl and benzoyl substituents being one to four of one or more groups selected from halogen, (lower)alkyl, halo(lower)alkyl, nitro, —$NR_4R_5$ or (lower)alkanoyl are prepared by reaction of compounds of formula I, wherein $R_1$ and $R_2$ are hydrogen and hydroxyl, with an alkali metal base (for example an alkali metal hydride, alkali metal hydroxide, alkali metal amide or alkali metal alcholate) and a benzyl halide or substituted benzyl halide or benzoyl halide or substituted benzoyl halide in an organic solvent, e.g., DMF, HMPTA, an aromatic hydrocarbon, e.g., benzene or toluene, or THF or a dioxane or a lower alkanol or ketone, e.g., acetone conveniently at a temperature of about 20°–30° C. In order to increase the yield of the desired compounds, an amount of the alkali metal base and benzyl halide or benzoyl halide in excess of the stoichiometric amount may be used.

The compounds of formula I thereby produced are isolated and purified utilizing known techniques such as by extraction, chromatography and recrystallization.

The especially suitable benzyl or benzoyl halides and substituted benzyl or benzoyl halides are commercially available or are made by synthetic procedures well known in the art.

Typical suitable substituted benzyl halides are the benzyl chlorides or bromides substituted by groups described in reference to the substituted benzyloxy groups above.

Typical suitable benzoyl halides include 2-, 3-, or 4-monohalo (e.g., chloro or fluoro) benzoyl chloride and 2,4-dihalo, 2,5-dihalo or 2,6-dihalo (e.g., 2,6-difluorobenzoyl chloride).

The compounds of the present invention wherein $R_3$ is —$CHR_7$—$CH(R_9)$ —$CH_2R_8$ may be prepared from compounds of the present invention represented by formulas I, Ia, Ib, Ic or Id wherein $R_3$ is —$CHR_7$—$C(R_9)=CHR_8$ by catalytic hydrogenation such as, for example with Pd/C. Compounds of the present invention wherein $R_3$ is —$CHR_7$—$C\equiv CR_8$ may be prepared from compounds of the present invention wherein $R_3$ is —$CH(R_7)$ —$C(R_9)=CHR_8$ by standard chemical reaction such as bromination/dehydrobromination such as for example with alcoholic KOH followed by $NaNH_2$.

Typical suitable $R_3$ groups include 2-propynyl, 2-propenyl, propyl, 1-methyl-2-propenyl, 2-methyl-2-propenyl, 1-methylpropyl, 2-butynyl, 2-butenyl, butyl, 1-methyl-2-butynyl, 1-methyl-2-butenyl, 2-methyl-2-butenyl, 2-ethyl-2-butenyl, 1-phenyl-2-propenyl, 2-phenyl-2-propenyl, 3-phenyl-2-propenyl, 3-phenyl-2-propynyl, 2-(4-fluorophenyl)-2-propenyl, 2-(4-chlorophenyl)-2-propenyl, 2-(2,4-difluorophenyl)-2-butenyl, 2-(2,4-dichlorophenyl)-butyl, 2-(4-nitro-3-trifluoromethyl)-2-propenyl, 2-piperazino-2-propenyl, 2-(N-acetylpiperazino)-2-butyl, 2-(N-propyl piperazino)-2-pentenyl, 2-(4-acetylpeperidino)-2-butenyl, 2-[N-(4-trifluoromethylphenyl)piperazino-2-propenyl and 2-benzyl-2-propenyl, 2(2-4-difluorobenzyl)-2-butenyl and the like. The cis- and trans- isomers, e.g. cis- and trans-2-butenyl are also contemplated. Preferred $R_3$ groups include propyl, 2-propenyl, 2-propynyl, 2-aryl-2-propenyl such as 2-(2,4-difluorophenyl)-2-propenyl and 2- heterocyclyl-2-propenyl such as 2-(N-acetylpiperazino)-2-propenyl.

GENERAL DESCRIPTION OF THE PHARMACEUTICAL COMPOSITION AND METHOD OF USE ASPECTS OF THE INVENTION

The compounds of this invention exhibit broad spectrum antifungal activity, in conventional antifungal screening tests, against human and animal pathogens, such as the following: Aspergillus, Candida, Geotrichum, Microsporum, Monosporium, Rhodotorula, Saccharomyces, Torulopsis and Trichophyton.

The compounds of this invention exhibit topical fungal activity in in vivo tests in animals that is superior to that for miconazole, a commercial product. For example, (±)-cis-2-allyl-6-chloro-2,3-dihydro-3-hydroxy-2-(1H-1-imidazolylmethyl)-benzo[b]thiophene, in a hamster vaginal Candida topical infection model is more potent than miconazole.

The present invention also provides a pharmaceutical composition comprising an effective antifungal amount of a compound represented by formula I or a pharmaceutically acceptable salt thereof and a pharmaceutically acceptable carrier or diluent.

The preferred pharmaceutically acceptable salts are nontoxic acid addition salts formed by adding to the compounds of the present invention about a stoichiometric amount of a mineral acid, such as HCl, HBr, H2SO4 or H3PO4, or of an organic acid, such as acetic, propionic, valeric, oleic, palmitic, stearic, lauric, benzoic, lactic, para-toluene sulfonic, methane sulfonic, citric, maleic, fumaric, succinic and the like.

The pharmaceutical compositions of the present invention may be adapted for oral, parenteral or topical administration. They are formulated by combining the compound of this invention, or an equivalent amount of a pharmaceutically acceptable salt thereof with any suitable, inert, pharmaceutically acceptable carrier or diluent. The preferred mode of administration is topical.

Examples of suitable compositions include solid or liquid compositions for oral administration such as tablets, capsules, pills, powders, granules, solutions, dragees, suspensions or emulsions. They may also be manufactured in the form of sterile solid compositions which can be dissolved in sterile water, physiological saline or some other sterile injectable medium immediately before use.

Topical dosage forms may be prepared according to procedures well known in the art, and may contain a variety of ingredients, excipients and additives. The formulations for topical use include ointments, creams, lotions, powders, aerosols, pessaries and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcium phosphate, or boric acid. Aqueous suspensions of the above powders may also be made. Solutions or emulsions may also be prepared using inert solvents which are preferably nonflammable, odorless, colorless and nontoxic, for example, vegetable oils, and isopropanol. Similarly, aerosol or non-aerosol sprays may be prepared using solutions or suspensions in appropriate solvents, e.g., difluorodichloromethane, for aerosols.

Parenteral forms to be injected intravenously, intramuscularly, or subcutaneously are usually in the form of a sterile solution, and may contain salts or glucose to make the solution isotonic.

Based on the greater in vivo topical potency for the compounds of this invention compared to miconazole, the dosages of the compounds of the present invention employed to combat a given fungal infection in animals, e.g., mammals, including humans, is generally somewhat less than the dosage requirements of present commercial products such as miconazole.

It will be appreciated that the actual preferred dosages of the compounds of the present invention or pharmaceutically acceptable salts thereof will vary according to the particular composition formulated, the mode of application and the particular situs, host and disease being treated. Many factors that modify the action of the drug will be taken into account by the attending clinician, e.g., age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

In general, the topical dosage for humans ranges from about 50 mg per day to about 800 mg per 10 g of carrier day, in single or divided doses, with about 100 mg to about 200 mg per 10 g of carrier day (about 1% to about 2%) being preferred.

In general, the oral dosage for human ranges from about 50 mg to about 800 mg per kilogram of body weight per day, in single or divided doses, with about 100 mg per kilogram to about 400 mg per kilogram per day being preferred.

In general, the parenteral dosage for humans ranges for about 5 mg per day to about 50 mg per day, in single or divided doses, with about 10 mg per day being preferred. The following Examples illustrate the invention.

PREPARATION 1: (±)-CIS-2,3-DIHYDRO-3-HYDROXY-2-(1H-1-IMIDAZOLYLMETHYL)BENZO[b]THIOPHENES (A) (±)-cis-6-Chloro-2,3-dihydro-3-hydroxy-2-(1H-1-imidazolylmethyl)benzo[b]thiopene (1) 3-Bromo-7-chlorothiochroman-4-one Dissolve 7-chlorothiochroman-4-one (10 g., 50.3 mmole) in chloroform (100 mL) and cool the solution to 0°–5° C. Add bromine (2.60 mL, 50.3 mmole) dropwise over a 10-minute period. Stir the reaction mixture at room temperature for one hour, then add chloroform (100 mL) and extract with 10% aqueous sodium sulfite (100 mL) followed by water (200 mL). Dry the chloroform solution over anhydrous magnesium sulfate, filter and evaporate in vacuo to a residue. Recrystallize the residue from cyclohexane to give 3-bromo-7-chlorothiochroman-4-one, mp 109°–110° C.

(2) 3-Bromo-7-chlorothiochroman-4-ol

Suspend 3-bromo-7-chlorothiochroman-4-one (59.6 g., 215 mmole) in methanol (500 mL), cool to 0°–5° C., and with stirring add sodium borohydride (8.18 g., 215 mmole) in three portions. After stirring the reaction mixture at room temperature for three hours, pour it into ice water (4 liters) and extract with chloroform (2 liters). Dry the chloroform solution over anhydrous magnesium sulfate, filter and evaporate in vacuo to a residue. Triturate the residue with chloroform/hexane to give 3-bromo-7-chlorothiochroman-4-ol, mp 141°–142° C.

(3) (±)-cis-6-Chloro-2,3-dihydro-3-hydroxy-2-(1H-1-imidazolylmethyl) benzo[b]thiophene Add 3-bromo-7-chlorothiochroman-4-ol (5.27 g., 18.8 mmole) and imidazole (12.8 g., 188 mmole) to acetonitrile (100 mL.), and reflux for 4 hours. Pour the reaction mixture into water (500 mL.), and extract with chloroform (500 mL.). Wash the organic layer with water (500 mL.), dry it over anhydrous magnesium sulfate, filter and evaporate in vacuo. Triturate the residue with anhydrous ether, filter and recrystallize from acetonitrile to give (±)-cis-6-chloro-2,3-dihydro-3-hydroxy-2-(1H-1-imidazolylmethyl)benzo[b]thiophene, m.p. 164°–165° C.

(B) In the procedure of above Preparation 1A (1–3), substitute for the 7-chlorothiochroman-4-one an equivalent quantity of each of the following:
(a) thiochroman-4-one,
(b) 6-chlorothiochroman-4-one,
(c) 8-chlorothiochroman-4-one,
(d) 5,7-dichlorothiochroman-4-one,
(e) 6,7-dichlorothiochroman-4-one,
(f) 6,8-dichlorothiochroman-4-one,
(g) 7-trifluoromethylthiochroman-4-one,
(h) 6-trifluoromethylthiochroman-4-one,
(i) 6-fluorothiochroman-4-one,
(j) 7-fluorothiochroman-4-one,
(k) 8-fluorothiochroman-4-one,
(l) 6,7-difluorothiochroman-4-one,
(m) 6-methylthiochroman-4-one,
(n) 7-isopropylthiochroman-4-one,
(o) 6-cyanothiochroman-4-one,
(p) 7-cyanothiochroman-4-one,
(q) 6-nitrothiochroman-4-one,
(r) 7-nitrothiochroman-4-one,
(s) 6-nitro-7-trifluoromethylthiochroman-4-one,
(t) 6-(2,6-difluorophenyl)-thiochroman-4-one,
(u) 7-(2,6-difluorophenyl)-thiochroman-4-one,
(v) 6-(2-chloro,6-fluorophenyl)-thiochroman-4-one,
(w) 7-(2,4,6-trifluorophenyl)-thiochroman-4-one,
to obtain, respectively, upon purification and separation into their respective cis and trans isomers,
(a) (±)-cis-2,3-dihydro-3-hydroxy-2-(1H-1-imidazolylmethyl) benzo[b]-thiophene,
(b) (±)-cis-5-chloro-2,3-dihydro-3-hydroxy-2-(1H-1-imidazolylmethyl) benzo[b]thiophene,
(c) (±)-cis-7-chloro-2,3-dihydro-3-hydroxy-2-(1H-1-imidazolylmethyl)benzo[b]thiophene,
(d) (±)-cis-4,6-dichloro-2,3-dihydro-3-hydroxy-2-(1H-1-imidazolylmethyl)benzo[b]thiophene,
(e) (±)-cis-5,6-dichloro-2,3-dihydro-3-hydroxy-2-(1H-1-imidazolylmethyl)benzo[b]thiophene,
(f) (±)-cis-5,7-dichloro-2,3-dihydro-3-hydroxy-2-(1H-1-imidazolylmethyl)benzo[b]thiophene,
(g) (±)-cis-2,3-dihydro-3-hydroxy-2-(1H-1-imidazolylmethyl)-6-trifluoromethylbenzo[b]thiophene.
(h) (±)-cis-2,3-dihydro-3-hydroxy-2-(1H-1-imidazolylmethyl)-5-trifluoromethylbenzo[b]thiophene,
(i) (±)-cis-2,3-dihydro-5-fluoro-3-hydroxy-2-(1H-1-imidazolylmethyl) benzo[b]thiophene,
(j) (±)-cis-2,3-dihydro-6-fluoro-3-hydroxy-2-(1H-1-imidazolylmethyl)benzo[b]thiophene,
(k) (±)-cis-2,3-dihydro-7-fluoro-3-hydroxy-2-(1H-1-imidazolylmethyl)benzo[b]thiophene,
(l) (±)-cis-5,6-difluoro-2,3-dihydro-3-hydroxy-2-(1H-1-imidazolylmethyl)benzo[b]thiophene,
(m) (±)-cis-2,3-dihydro-3-hydroxy-2-(1H-1-imidazolylmethyl)-5-methylbenzo[b]thiophene,
(n) (±)-cis-2,3-dihydro-3-hydroxy-2-(1H-1-imidazolylmethyl)-6-isopropylbenzo[b]thiophene
(o) (±)-cis-5-cyano-2,3-dihydro-3-hydroxy-2-(1H-1-imidazolylmethyl)benzo[b]thiophene,
(q) (±)-cis-2,3-dihydro-3-hydroxy-2-(1H-1-imidazolylmethyl)-5-nitrobenzo[b]thiophene,
(r) (±)-cis-2,3-dihydro-3-hydroxy-2-(1H-1-imidazolylmethyl)-6-nitrobenzo[b]thiophene,
(s) (±)-cis-2,3-dihydro-3-hydroxy-2-(1H-1-imidazolylmethyl)-5-nitro-6-trifluoromethylbenzo[b]thiophene,
(t) (±)-cis-5-(2,6-difluorophenyl)-2,3-dihydro-3hydroxy-2-(1H-1-imidazolylmethyl)benzo[b]thiophene,
(u) (±)-cis-6-(2,6-difluorophenyl)-2,3-dihydro-3-hydroxy-2-(1H-1-imidazolylmethyl)benzo[b]thiophene,
(v) (±)-cis-5-(2-chloro-6-fluorophenyl)-2,3-dihydro-3-hydroxy-2-(1H-1-imidazolylmethyl)benzo[b]thiophene,
(w) (±)-cis-2,3-dihydro-3-hydroxy-2-(1H-1-imidazolylmethyl)-6-(2,4,6-trifluorophenyl)benzo[b]thiophene,
and the trans isomers thereof.

EXAMPLE 1

(±)-cis-3-Allyloxy-6-chloro-2,3-dihydro-2-(1H-1- 0 imidazolylmethyl)benzo[b]thiophene-1-oxide

A.

(±)-cis-3-Allyloxy-6-chloro-2,3-dihydro-2-(1H-1-imidazolylmethyl) benzo[b]thiophene Stir a mixture of 3.0 g (0.01 moles) of (±)cis-6-chloro-2,3-dihydro-2-(1H-1-imidazolylmethyl)benzo[b]-thiophene, 3.44 g (0.045 mole) of allyl chloride, 25 mL of 50 wgt % sodium hydroxide and 3 drops of tricaprylylmethylammonium chloride in 50 mL of THF overnight. Dilute the reaction mixture with 300 mL of methylene chloride. Separate the organic layer and wash it with water, and dry over anhydrous magnesium sulfate. Evaporate the organic solvents to give 3.2 g of the title compound, m/e of the molecular ion, 306 (hereinafter "m/e").

B.

(±)-cis-3-Allyloxy-6-chloro-2,3-dihydro-2-(1H-1-imidazolymethyl) benzo[b]thiophene-1-oxide Dissolve 21.7 g. (70.7 mmole) of (±)-cis-3-allyloxy-6-chloro-2,3-dihydro-2-(1H-1-imidazolylmethyl) benzo[b]thiophene in 500 mL of CH$_2$Cl$_2$ and cool the solution to 0°–5°. Added 14.6 g (70.7 mmole) of m-chloroperoxybenzoic acid (tech. 80–85%) and stir the reaction mixture at 0°–5° for 1 hour. Extract the reaction mixture with 500 mL of 5% aqueous NaHCO$_3$ followed by 500 mL of H$_2$O. Dried the CH$_2$Cl$_2$ layer over anhydrous MgSO$_4$ and concentrate it to give (±)-cis-3-allyloxy-6-chloro-2,3-dihydro-2-(1H-1-imidazolylmethyl)benzo[b]thiophene-1-oxide, a gum, m/e 322.

EXAMPLE 2

(±)-2-Allyl-6-chloro-2,3-dihydro-2-(1H-1-imidazolylmethyl)benzo[b]thiophene-3-one Reflux 15.2 g (47.1 mmole) of cis 3-allyloxy-6-chloro-2,3-dihydro-2-(1H-1-imidazolylmethyl)benzo[b]thiophene-1-oxide and 9.97 mL (70.6 mole) of trifluoroacetic anhydride in 150 mL of toluene for 1 hr. Pour the reaction mixture into 1 liter of CHCl$_3$ and extract it with 1 liter of 5% aqueous Na₂CO₃ followed by 1 liter of H₂O. Dry the organic layer over anhydrous MgSO₄ and evaporate the solvent in vacuo. Chromatograph the oily residue on 500 g of silica gel eluting with CHCl₃ to give 2-allyl-6-chloro-2,3-dihydro-2-(1H-1-imidazolylmethyl) benzo[b]thiophene-3-one, a gum, m/e 304.

EXAMPLE 3

(±) cis-and (±)-trans-2-Allyl-6-chloro-2,3-dihydro-3-hydroxy-2-(1H-1-imidazolylmethyl)benzo[b]thiophene Suspend 10.2 g (33.5 mmole) of 2-allyl-6-chloro-2,3-dihydro-2-(1H-1-imidazolylmethyl)benzo[b]thiophene-3-one in 150 mL of methanol and cool the mixture to 0°-5° C. Add 1.27 g (33.5 mmole) of NaBH₄. Allow the temperature to slowly rise to RT over 3 hrs. Pour the reaction mixture into 1 liter of CHCl₃ and wash it with 2-1 liter portions of H₂O. Dry the organic layer over anhydrous MgSO₄ and evaporate the solvent in vacuo. Recrystallize the residue from CH₃CN to give a mixture of (±)-cis and (±) trans -2-allyl-6-chloro-2,3-dihydro-3-hydroxy-2-(1H-1-imidazolylmethyl)benzo[b]thiophene, m/e 306. Found: C 58.74, H 4.91, N 9.37, Cl 11.44, S 10.64. Calculated for $C_{15}H_{15}ClN_2OS$: 58.72, H 4.93, N 9.13, Cl 11.55, S 10.45.

Fractionally crystallize the mixture of (±)-cis and (±)-trans isomers from acetonitrile to give the (±) cis isomer of the title compound (mp 168° C.; m/e 306) and a mother liquor which provided the (±) trans isomer of the title compound (mp 130°-132° C., m/e 306).

EXAMPLE 4

(±)-cis-and(±)-trans-6-Chloro-2,3-dihydro-3-hydroxy-2-(1H-1-imidazolylmethyl)-2-[2-(4-chlorophenyl)-2-propenyl]benzo[b]thiophene

A.

(±)-cis-6-Chloro-2,3-dihydro-2-(1H-1-imidazolylmethyl)-3-[2-(4-chlorophenyl)-2-propenyloxy]benzo[b]thiophene Dissolve 2.665 g (10 mmole) of the compound of Preparation 1(A)(3) in 50 mL of THF and 25 mL of 50% aqueous NaOH. To the solution so formed, add, with stirring, 2.315 g (10 mmole) of α-bromomethyl-4-chlorostyrene and 3–5 drops of tricaprylylmethyl ammonium chloride. Continue to stir the reaction mixture so formed overnight at room temperature and add 500 mL of CHCl₃. Wash the organic layer with water until the pH of the aqueous layer is about 7. Dry the organic layer over anhydrous magnesium sulfate, filter and evaporate in vacuo to a residue. Chromatograph the residue on a silica gel column, eluting with CHCl₃ to give the title compound, m/e 417.

B.

(±)-cis-6-Chloro-2,3-dihydro-2-(1H-1-imidazolylmethyl)-3[2-(4-chlorophenyl)-2-propenyloxy]benzo[b]thiophene-1-oxide Add 1.61 g (9.32 mmole) of m-chloroperbenzoic acid to a solution of 2.50 g (5.7 mmole) of the compound of Example 4A in 100 mL of CH₂Cl₂. Stir the reaction mixture at room temperature for 2 hours. Wash the reaction mixture with 5% aqueous sodium bicarbonate and water. Dry the organic layer over anhydrous magnesium sulfate, filter and evaporate in vacuo to give the title compound as a gum, m/e 433.

C.

(±)-6-Chloro-2,3-dihydro-2-(1H-1-imidazolylmethyl)-2-[2-(4-chlorophenyl)-2-propenyl]benzo[b]thiophene-3-one Reflux a solution of 2.50 g (5.7 mmole) of the compound of Example 4B and 2.42 g (11.5 mmole) of triflouroacetic anhydride in 100 mL of toluene for 1 hour. Evaporate the solution to dryness and dissolve the residue with methylene chloride. Wash the solution so formed with water. Dry the solution over anhydrous magnesium sulfate, filter and evaporate to give a gum. Chromatograph the gum on a silica gel column, eluting with CHCl₃ to give the title compound as an oil, m/e 416.

D.

(±)-cis-and (±)-trans-6-Chloro-2,3-dihydro-3-hydroxy-2-(1H-1-imidazolylmethyl)-2-[2-(4-chlorophenyl)-2-propenyl]benzo[b]thiophene Dissolve 0.700 g (1.69 mmole) of the compound of Example 4C in 25 mL of methanol and cool the solution so formed to 0° C. Add, with stirring, 0.064 g (1.69 mmole) of NaBH₄. Continue stirring at 0° C. for 2 hours. Evaporate the methanol and dissolve the residue in 500 mL of CHCl₃. Wash the CHCl₃ solution over anhydrous magnesium sulfate, filter and evaporate to give a residue. Purify the residue by flash chromatography on silica gel (TLC grade), eluting with ethyl acetate to give a solid. Crystallize the solid from ethyl acetate to give the title compound (a mixture of cis and trans isomers) as an off-white solid, mp 165°-168° C., m/e 418.

EXAMPLE 5

(±)-cis-2-Allyl-6-chloro-3-(2-chloro-6-fluorobenzyloxy)-2,3-dihydro-2-(1H-1-imidazolylmethyl)benzo[b]thiophene Dissolve 1.0 g (3.20 mmole) of the (±)-cis-isomer of Example 3 in 10 mL of dimethylformamide (DMF). Add 0.313 g (6.52 mmole) of 50% dispersion of sodium hydride in mineral oil and stir the reaction mixture so formed for 30 minutes at room temperature. Add 0.83 mL (6.52 mmole) of 2-chloro-6-fluorobenzyl chloride (Aldrich Chemical Co.) and stir the reaction mixture so formed for 1 hour at room temperature. Pour the mixture into 500 mL of diethyl ether and 500 mL of water. Stir for 5 minutes. Separate the layers and wash the organic layer with water. Dry the organic layer over anhydrous magnesium sulfate and evaporate in vacuo to give a gum. Chromatograph the gum on silica gel, eluting with CHCl₃ to give the title compound as a gum, m/e 448.

EXAMPLE 6

(±)-cis-2-Allyl-3-(2-chloro-6-fluorobenzyloxy)-2,3-dihydro-5-fluoro-2-(1H-1-imidazolylmethyl)benzo[b]thiophene

A.

(±)-3-Allyloxy-2,3-dihydro-5-fluoro-2-(1H-1-imidazolylmethyl) benzo[b]thiophene

Follow the procedure of Example 4A except substitute equivalent quantities of (±)-cis-2,3-dihydro-6-fluoro-3-hydroxy-2-(1H-1-imidazolylmethyl)benzo[b]thiophene (Preparation 1(B)(c) and allyl bromide for the compound of Preparation 1(A)(3) and α- bromomethyl-4-chlorostyrene, respectively to give the title compound of this Example.

B. (±)-cis-3-Allyloxy-2,3-dihydro-5-fluoro-2,3-dihydro-2-(1H-1-imidazolylmethyl)benzo[b]thiophene-1-oxide Follow the procedure of Example 4B except substitute an equivalent quantity of the title compound of Example 6A for (±)-cis-6-chloro-2,3-dihydro-2-(1H-1-imidazolylmethyl)-3-[2-(4-chlorophenyl)-2-propenyloxy]benzo[b]thiophene to give the title compound of this Example.

C. (±)-cis-and (±)-trans-2-Allyl-2,3-dihydro-5-fluoro-3-hydroxy-2-(1H-1-imidazolylmethyl)benzo[b]thiophene Follow the procedure of Example 4C but substitute an equivalent quantity of the compound of Example 6B for the title compound of Example 4C to give the corresponding benzo[b]thiophene-3-one which is thereafter treated in accordance with the procedure of Example 4D to provide the mixture of (±)-cis and (±)-trans-isomers of the title compound of this Example. Fractionally crystallize the mixture to obtain the title compound of this Example as well as the corresponding (±)-trans isomer.

D. (±)-cis-2-Allyl-3-(2-chloro-6-fluorobenzyloxy)-2,3-dihydro-5-fluoro-2-(1H-1-imidazolylmethyl)benzo[b]thiophene Dissolve 2.0 g (6.89 mmoles) of the (±)-cis isomer of title compound of Example 6C in 50 mL of DMF. Add, with stirring, 0.662 g (13.8 mmoles) of sodium hydride (a 50% dispersion in mineral oil) and continue stirring the slurry so formed at room temperature for 30 minutes. Add 1.31 mL (10.3 mmoles) of 2-chloro-6-fluorobenzyl chloride and continue stirring at room temperature for 1 hour. Pour the reaction mixture into a mixture of 1 liter of ethyl ether and 1 liter of water. Stir the mixture so formed for 10 minutes. Separate the layers and wash the organic layer with 1 liter of water. Dry the organic layer over anhydrous magnesium sulfate, filter and evaporate in vacuo to give a residue. Chromatograph the residue or silica gel, eluting with $CHCl_3$ to give the title compound as a gum, m/e 432.

EXAMPLE 7

(±)-2-Allyl-3,6-dichloro-2,3-dihydro-2-(1H-1-imidazolylmethyl)benzo[b]thiophene

Heat a solution of 2 g (6.5 mmoles) of the (±)-cis isomer of Example 3 and 3.38 g (32.6 mmoles) of thionylchloride in 50 mL of benzene at reflux for 2 hours. Evaporate the reaction mixture to dryness to give the title compound as a gum, m/e 324.

EXAMPLE 8

(±)-2-Allyl-6-chloro-2,3-dihydro-3-fluoro-2-(1H-1-imidazolylmethyl) benzo[b]thiophene Dissolve 1.0 g (3.25 mmoles) of the (±)-cis isomer of Example 3 in 50 mL of tetrahydrofuran and cool the solution to 0°–5° C. Add, with stirring, 1.06 g (6.50 mmoles) of diethylaminosulfur trifluoride ("DAST", obtained from Aldrich Chemical Co.) and continue to stir the reaction mixture for 1 hour. Evaporate the reaction mixture to give a residue. Triturate the residue with methylene chloride and wash the organic solution so formed with water. Dry the organic layer over anhydrous magnesium sulfate, filter and evaporate to give the title compound, m/e 308.

EXAMPLE 9

(±)-cis and (±)-trans-2-Allyl-6-chloro-2,3-dihydro-3-(1H-imidazolyl)-2-(1H-1-imidazolylmethyl)benzo[b]thiophene

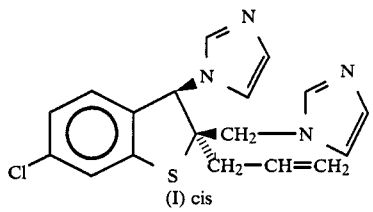
(I) cis

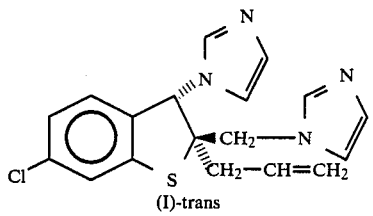
(I)-trans

Heat a solution of 2.0 g (6.1 mmoles) of the title compound of Example 7 and 0.9 g (13.2 mmoles) of imidazole in 50 mL of DMF at 100° C. overnight. Evaporate the solution to a residue. Triturate the residue with $CHCl_3$ and wash the $CHCl_3$ solution with water. Dry the organic layer over anhydrous magnesium sulfate, filter and evaporate to give a residue. Chromatograph the residue on silica gel, eluting with 1:99 (v/v) $CH_3OH:CHCl_3$ to give the cis and trans isomers of the title compound as gums, m/e 357 for each isomer.

EXAMPLE 10

(±)-2-Allyl-6-chloro-2,3-dihydro-2-(1H-1-imidazolylmethyl)benzo[b]thiophene

Heat a reaction mixture of 1.4 g (4.3 mmoles) of the title compound of Example 7 and 2.5 g (8.5 mmoles) of tri(n-butyl)tin hydride in 20 mL of toluene at reflux overnight. Evaporate to give a residue. Chromatograph the residue on silica gel, eluting with 1:1 (v/v) ethyl acetate:hexane to give the title compound as an oil, m/e 290.

EXAMPLE 11

(±)-cis-N,N-Dimethyl-O-[2-allyl-6-chloro-2-(1H-1-imidazolylmethyl) benzo[b]thiophene-3-yl]thiocarbamate Dissolve 1.0 g (3.2 mmoles) of the (±)-cis isomer of the title compound of Example 3 in 25 mL of DMF. Add, with stirring, 0.086 g (3.58 mmoles) of sodium hydride, (as a 50% dispersion in mineral oil) and continue stirring at room temperature for 1 hour. Add to the stirred solution 0.6 g (4.85 mmoles) of dimethylthiocarbamoyl chloride (Aldrich Chemical Co.) and continue to stir the reaction mixture so formed overnight. Evaporate the reaction mixture to a residue. Triturate the residue with methylene chloride. Wash the organic layer with water. Dry the organic layer over anydrous magnesium sulfate, filter and evaporate to give an oil. Chromatograph the oil on silica gel, eluting with 1:99

(v/v) CH₃OH:CHCl₃ to give the title compound as a gum, m/e 394.

EXAMPLE 12

(±)-cis and (±)-trans-2-Allyl-2,3-dihydro-3-hydroxy-2-(1H-1-imidazolylmethyl)benzo[b]thiophenes Follow the procedure of Example 4A except substitute equivalent quantities of each of the (±) cis-2,3-dihydro-3-hydroxy-2-(1H-1-imidazolylmethyl)benzo[b]thiophene compounds a-v obtained in Preparation 1B for the compound of Preparation 1(A)(3) and allyl chloride for α-bromomethyl-4-chlorostyrene. There is obtained the corresponding 3-allyloxy derivatives of each of the foregoing, which upon reaction with m-chloroperbenzoic acid according to the procedure of Example 4B provides the corresponding benzo[b]thiophene-1-oxide derivatives which are treated with trifluoroacetic anhydride and thereafter with NaBH₄ in accordance with the procedures of Examples 4C and D to provide a mixture of (±)-cis and (±)-trans isomers which is separated into the (±)-cis isomers, (a) (±)-cis-2-Allyl-2,3-dihydro-3-hydroxy-2-(1H-1-imidazolylmethyl)benzo[b]thiophene,
(b) (±)-cis-2-Allyl-5-chloro-2,-3-dihydro-3-hydroxy-2-(1H-1-imidazolylmethyl)benzo[b]thiophene,
(c) (±)-cis-2-Allyl-7-chloro-2,3-dihydro-3-hydroxy-2-(1H-1-imidazolylmethyl)benzo[b]thiophene,
(d) (±)-cis-2-Allyl-4,6-dichloro-2,3-dichydro-3-hydroxy-2-(1H-1-imidazolylmethyl)benzo[b]thiophene,
(e) (±)-cis-2-Allyl-5,6-dichloro-2,3-dihydro-3-hydroxy-2-(1H-1-imidazolylmethyl)benzo[b]thiophene,
(f) (±)-cis-2-Allyl-5,7-dichloro-2,3-dihydro-3-hydroxy-2-(1H-1-imidazolylmethyl)benzo[b]thiophene,
(g) (±)-cis-2-Allyl-2,3-dihydro-3-hydroxy-2-(1H-1-imidazolylmethyl)-6-trifluoromethylbenzo[b]-thiophene,
(h) (±)-cis-2-Allyl-2,3-dihydro-3-hydroxy-2-(1H-1-imidazolylmethyl)-5-trifluoromethylbenzo[b]-thiophene,
(i) (±)-cis-2-Allyl-2,3-dihydro-5-fluoro-3-hydroxy-2-(1H-1-imidazolylmethyl)benzo[b]thiophene,
(j) (±)-cis-2-Allyl-2,3-dihydro-6-fluoro-3-hydroxy-2-(1H-1-imidazolylmethyl)benzo[b]thiophene,
(k) (±)-cis-2-Allyl-2,3-dihydro-7-fluoro-3-hydroxy-2-(1H-1-imidazolylmethyl)benzo[b]thiophene,
(l) (±)-cis-2-Allyl-5-6,difluoro-2,3-dihydro-3-hydroxy-2-(1H-1-imidazolylmethyl)benzo[b]thiophene,
(m) (±)-cis-2-Allyl-2,3-dihydro-3-hydroxy-2-(1H-1-imidazolylmethyl)-5-methylbenzo[b]thiophene,
(n) (±)-cis-2-Allyl-2,3-dihydro-3-hydroxy-2-(1H-1-imidazolylmethyl)-6-ispropylbenzo[b]thiophene,
(o) (±)-cis-2-Allyl-5-cyano-2,3-dihydro-3-hydroxy-2-(1H-1imidazolylmethyl)benzo[b]thiophene,
(p) (±)-cis-2-Allyl-6-cyano-2,3-dihydro-3-hydroxy-2-(1H-1-imidazolylmethyl)benzo[b]thiophene,
(q) (±)-cis-2-Allyl-2,3-dihydro-3-hydroxy-2-(1H-1-imidazolylmethyl)-5-nitrobenzo[b]thiophene,
(r) (±)-cis-2-Allyl-2,3-dihydro-3-hydroxy-2-(1H-1-imidazolylmethyl)-6-nitrobenzo[b]thiophene,
(s) (±)-cis-2-Allyl-2,3-dihydro-3-hydroxy-2-(1H-1-imidazolylmethyl)-5-nitro-6-trifluoromethyl-benzo[b]thiophene,
(t) (±)-cis-2-Allyl-5-(2,6-difluorophenyl)-2,-dihydro-3-hydroxy-2-(1H-1-imidazolylmethyl)benzo[b]thiophene,
(u) (±)-cis-2-Allyl-6-(2,6-difluorophenyl)-2,3-dihydro-3-hydroxy-2-(1H-1-imidazolylmethyl)benzo[b]thiophene,
(v) (±)-cis-2-Allyl-2,3-dihydro-3-hydroxy-2-(1H-1-imidazolylmethyl)-6-(2,4,6-trifluorophenyl)benzo[b]thiophene, and the trans isomers thereof.

EXAMPLE 13

(±)-cis-and (±)-trans-2-Allyl-2,3-dihydro-5-fluoro-3-hydroxy-2-(1H-1,2,4-triazol-1-ylmethyl)benzo[b]thiophene Follow the procedure of Example 4A except substitute equivalent quantities of (±)-cis-2,3-dihydro-5fluoro-3-hydroxy-2-(1H-1,2,4-triazol-1-ylmethyl)-benzo[b]thiophene for the compound of preparation 1(A)(3) and of allyl chloride for α-bromoethyl-4-chlorostyrene. There is obtained the corresponding 3-allyloxy derivative which upon reaction with m-chloroperbenzoic acid according to the procedure of Example 4B provides the corresponding benzo[b]thiophene-1-oxide derivative which is treated with trifluoroacetic anhydride and thereafter with NaBH₄ in accordance with the procedures of Example 4C and 4D to provide a mixture of the (±)-cis and (±)-trans- isomers which is separated by fractional crystallization into the title compounds, mp 149°–150° C. and 157°–159° C., respectively, both white solids.

EXAMPLE 14

(±)-cis- and (±)-trans-2-Allyl-2,3-dihydro-5-fluoro-3-hydroxy-2-(1H-1,2,4-triazol-1-ylmethyl)benzo[b]thiophene Follow the procedure of Example 13 except substitute an equivalent quantity of (±)-cis-2,3-dihydro-5-fluoro-3-hydroxyl-2-(1H-1,2,4-triazol-1-ylmethyl)benzo[b]thiophene for the compound of Preparation 1(A)(3) (which in turn is prepared by following procedure of Preparation 1(A)(3) by substituting an equivalent quantity of 1H-1,2,4-triazole for imidazole). The mixture of (±)-cis and trans-isomers is separated by fractional crystallization into the title compounds.

EXAMPLE 15

(±)-cis- and (±)-trans-2-Allyl-6-chloro-2,3-dihydro-2-(1H-1-imidazolylmethyl)-3-(2,4-dichlorobenzoyloxy)benzo[b]thiophene Stir a mixture of 1 g (3.2 mmoles) of the title compounds of Example 3, 1.36 g (6.49 mmoles) of 2,4-dichlorobenzoyl chloride and 0.66 (6.52 mmoles) of trimethylamine in 50 mL of methylene chloride at room temperature for 4 hours. Dilute the reaction mixture with water. Separate the organic phase and wash the organic phase with 5 wgt % sodium bicarbonate and then with water. Dry over anhydrous magnesium sulfate and evaporate the organic solvent to give an oil. Chromatograph the oil on a silica gel column, eluting with chloroform to give the (±)-cis and -trans isomers of the title compound, each having m/e 479.

EXAMPLE 16

(±)-cis-and (±-trans-2-allyl-6-chloro-3-[(4-chlorophenoxy)ethoxy]-2,3-dihydro-2-(1H-1-imidazolylmethyl) benzo[b]thiophene Add 0.086 g (3.43 mmoles) of sodium hydride 50% oil dispersion to a solution of 1 g (3.2 mmoles) of the title compounds of Example 3 in 20 mL of DMSO stir slurry so formed for 1 hour and add thereto 1.63 g (6.5 mmoles) of 1-(4-chlorophenoxy)-2-mesylethane. Heat the reaction mixture overnight. Extract the reaction mixture with methylene chloride. Wash the organic layer with water and dry it over anhydrous $MgSO_4$. Evaporate the solvent to give a gum. Chromatograph the gum on a silica gel column, eluting the chloroform to give 278 mg of the title compounds as an oil, m/e 461.

EXAMPLE 17

(±)cis-and(±)-trans-2-Allyl-6-chloro-2,3-dihydro-2-(1H-1-imidazolylmethyl)-3-(1H-1,2,4-triazolylmethoxy)benzo[b]thiophene Add 0.96 g (20 mmoles) of sodium hydride (50% oil dispersion) to a solution of 1.0 g (3.26 mmoles) of the title compounds of Example 3 in 10 ml of DMF. Stir for 30 minutes at RT. Add dropwise a solution of 2.43 g (10 mmoles) of 1-bromomethyl-1,2,4-triazole hydrogen bromide in 10 mL of DMF. Stir the reaction mixture so formed overnight at RT. Pour the reaction mixture into 500 mL of $CHCl_3$ and 500mL of brine and stir for 10 minutes. Separate and dry the organic layer over anhydrous $MgSO_4$. Remove the organic solvent in vacuo to give an oily residue. Chromatograph the oily residue on silica gel, eluting with 1:99 (vv) MeOH: $CHCl_3$ containing 1% (v/v) of conc. $NH_4OH$ to give 0.75 g of the title compounds, m/e 387

EXAMPLE 18

(±)-cis-and(±)-trans-2-Allyl-3-allyloxy-6-chloro-2,3-dihydro-2-(1H-1-imidazolylmethyl)benzo[b]thiophene Add 0.32 mL (3.66 mmoles) of allyl bromide and two drops of tricaprylylmethylammonium chloride to a solution of 0.75 g (2.44 mmoles) of the title compounds of Example 3 and 10 mL of 50% of NaOH in 30 mL of THF. Stir the reaction mixture (at RT for 3 hours. Pour the reaction mixture into 250 mL of $CHCl_3$ and 250 mL of brine and stir for 5 minutes. Separate and dry the organic layer over anhydrous $MgSO_4$. Remove the organic solvent in vacuo to give an oily residue. Chromatograph the oily residue on a silica gel column, eluting with $CHCl_3$ to give 0.83 g of the title compounds, m/e 346.

EXAMPLE 19

(±)-cis-and (±)-trans-2-Allyl-3-allyloxy-5-fluoro 3-(1H-1,2,4-triazoylmethoxy)-2-(1H-1,2,4-triazolylmethyl)benzo[b]thiophene Add 0.96 g (20 mmoles) of sodium hydride (50% oil dispersion) to a solution of 0.895 g (3.07 mmoles) of the title compounds of Example 13 in 10 mL of DMF and stir for 30 minutes at RT. Add dropwise thereto a solution of 2.43 g (1.0 mmoles) of 1-bromomethyl-1H-1,2,4-triazole hydrogen bromide in 10 mL of DMF. Stir the reaction mixture for 1 hour at RT. Pour the reaction mixture into 500 mL of $CHCl_3$ and 500 mL of brine. Separate and dry the organic layer over anhydrous $MgSO_4$. Remove the organic solvents in vacuo to give an oily residue. Chromatograph the oily residue on a silica gel column, eluting with 1:99 (v/v) MeOH: $CHCl_3$ containing 1 volume % of concentrated $NH_4OH$ to give 1.04 g of the title compounds, m/e 372.

EXAMPLE 20

(±)-cis-and (±)-trans-2-Allyl-2,3-dihydro-3-[1-(3,3-dimethyl-1-butynyl)]-5-fluoro-3-hydroxy-2-(1H-1,2,4-triazolylmethyl)benzo[b]thiophene Add 12.0 mL (18.6 mmoles) of n-butyl lithium (1.55 M in hexane) to a solution of 2.0 mL (16.2 mmoles) of 3,3-dimethyl-1-butyne in 50 mL of dry THF at a temperature of 0°-5° C. Stir for 30 minutes at 0°-5° C. Add thereto 2.0 g (6.92 mmoles) of the title compounds of Example 14. Stir the reaction mixture so formed overnight at RT. Pour the reaction mixture into 1 L of $CHCl_3$. Wash the organic layer with 1 L of brine. Separate and dry the organic layer over anhydrous $MgSO_4$. Remove the organic solvents in vacuo to give a gum. Chromatograph the gum on a silica gel column, eluting with $CHCl_3$ to give 0.429 g of the less polar isomer of the title compounds, as a solid, mp 166°-167° C., m/e 369 and 0.541 g of the more polar isomer of the title compounds as a gum, me/e 369.

EXAMPLE 21

(±)-cis-and (±)-trans-2-Allyl-2,3-dihydro-6-fluoro-3-hydroxy-2-(1H-1-imidazolylmethyl)benzo[b]thiophene Add 4.1 mL (11.6 mmoles) of 2.8 M $CH_3MgBr$ to a suspension of 1.67 g (5.79 mmoles) of the compounds of Example 12(j) in 25 mL of THF. Stir the reaction mixture for 1 hour at RT and then heat at reflux for 2 hours. Add 25 mL of 10% $NH_4Cl$ and stir for 10 minutes. Pour into 500 mL of $CHCl_3$ and 500 mL of brine. Remove the solvent in vacuo to give an oily residue. Chromatograph the oily residue on a silica gel column, eluting with 1:99 (v/v) MeOH: $CHCl_3$ containing 1 vol.% of conc. $NH_4OH$ to give 0.281 g of the less polar isomer of the title compounds, m/e 304 and 0.303 g of the more polar isomer, m/e 304.

FORMULATIONS

The following are typical pharmaceutical formulations containing as the active ingredient (designated "Drug") the compound of this invention such as (±)-cis-2-allyl-6-chloro-2,3-dihydro-3-hydroxy-2-(1H-1-imidazolylmethyl) benzo[b]thiophene or (±)-cis-2-allyl-6-chloro-3-(2-chloro-6-fluorobenzyloxy)-2,3-dihydro-2-(1H-1-imidazolylmethyl)benzo[b]-thiophene. It will be appreciated, however, that either of these compounds may be replaced by equally effective quantities of other compounds of this invention.

| FORMULATION 1 | |
|---|---|
| Tablet 125.00 mg. tab. | |
| Drug | 125.00 mg. |
| Polyethylene glycol 6000 | 100.00 mg. |
| Sodium lauryl sulfate | 6.25 mg. |
| Corn starch | 30.00 mg. |
| Lactose, anhydrous | 87.25 mg. |
| Magnesium stearate | 1.50 mg. |

PROCEDURE

Heat the polyethylene glycol 6000 to 70°–80° C. Mix the drug, sodium lauryl sulfate, corn starch, and lactose into the liquid and allow the mixture to cool. Pass the solidified mixture through a mill. Blend granules with magnesium stearate and compress into tablets.

| FORMULATION 2 | |
| --- | --- |
| Capsule 250 mg. tab. | |
| Drug | 250.00 mg. |
| Lactose, anhydrous | 100.00 mg. |
| Corn starch | 50.00 mg. |
| Microcrystalline cellulose | 95.00 mg. |
| Magnesium stearate | 5.00 mg. |

PROCEDURE

Mix the first four ingredients in a suitable mixer for 10–15 minutes. Add the magnesium stearate and mix for 1–3 minutes. Fill the mixture into suitable two-piece hard gelatin capsules using an encapsulating machine.

What is claimed is:

1. A compound represented by the formula I

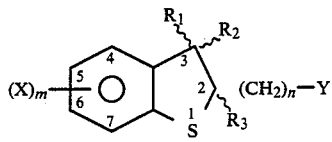

in racemic or optically active form, or a pharmaceutically acceptable salt thereof wherein X is one or more groups selected independently from halogen, (lower)alkyl, halo(lower)alkyl, cyano, nitro, substituted and unsubstituted phenyl or substituted and unsubstituted phenyl(lower)alkyl, said phenyl and phenyl(lower)alkyl substituents being one to four of one or more groups independently selected from halogen, nitro, $-NR_4R_5$, (lower)alkanoyl, (lower)alkyl or halo(lower)alkyl;

Y is substituted or unsubstituted imidazolyl or 1,2,4-triazolyl, said substituents being one or more groups selected independently from (lower) alkyl, substituted and unsubstituted phenyl or substituted and unsubstituted phenyl(lower)alkyl, said substituents being as described hereinabove;

$R_1$ and $R_2$ are independently hydrogen, $-CH_2NR_4R_5$, $-NR_4R_5$, $-OR_4$, $-SR_5$, (lower)alkyl, (lower)alkenyl, halogen, substituted or unsubstituted phenyl or phenyl(lower)alkyl, said phenyl and phenyl(lower)alkyl substituents being as described hereinabove, or $R_1$ or $R_2$ taken together with the carbon in the 3 position form carbonyl, thiocarbonyl, $>C=N-R_4$,

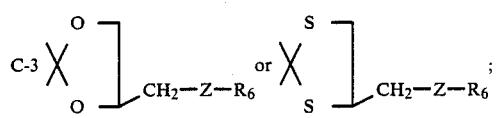

$R_3$ is $-CH-C\equiv CR_8$, $-CH-C=CHR_8$ or
  |                |  |
  $R_7$           $R_7$ $R_9$ $$-CH-CH-CH_2R_8;$$
$$\;\;\;|\;\;\;\;\;|$$
$$\;R_7\;\;R_9$$

and $R_6$, $R_7$, $R_8$ and $R_9$ are independently hydrogen, (lower)alkyl, substituted or unsubstituted phenyl or phenyl(lower)alkyl, said phenyl or phenyl(lower)alkyl substituents being as described hereinabove, or substituted or unsubstituted five or six membered heterocyclyl ring systems containing carbon and one to four heterto atoms chosen from N, O and S, said heterocyclyl substituents being halogen, lower(alkyl), (lower)alkanoyl, substituted and unsubstituted phenyl or substituted and unsubstituted phenyl(lower alkyl), said phenyl and phenyl(lower)alkyl substituents being asd described hereinabove;

$R_4$ and $R_5$ are independently hydrogen, lower(alkyl), (lower)alkenyl, N,N-di(lower)alkylcarbamoyl, N,N-di(lower)alkylthiocarbamoyl, substituted and unsubstituted phenylcarbonyl or substituted and unsubstituted phenyl(lower)alkylcarbonyl, substituted or unsubstituted phenyl and phenyl(lower)alkyl, said phenyl and phenyl(lower)alkyl substituents being as described hereinabove, or $R_4$ and $R_5$ taken together with the nitrogen atom in $NR_4R_5$ and $-CH_2-NR_4R_5$ form substituted or unsubstituted five or six membered heterocyclyl ring systems containing carbon and one to four heteroatoms chosen from N, O and S, said heterocyclyl substituents being as described hereinabove;

Z is O, S or $NR_5$;

N=1 or 2; and m=1, 2, 3 or 4.

2. A compound of claim 1 wherein $R_1$ and $R_2$ are independently hydrogen and hydroxyl.

3. A compound of claim 1 wherein $R_3$ and $R_4$ are hydrogen.

4. A compound of claim 1 wherein n is 1.

5. A compound of claim 1 wherein Y is imidazolyl.

6. A compound of claim 1 wherein $R_3$ is

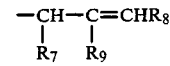

7. A compound of claim 1 which is 2-allkyl-6-chloro-2,3-dihydro-3-hydrdoxy-2-(1H-1-imidazolylmethyl) benzo[b]thiophene.

8. A compound of claim 7 wherein the 3-hydroxy and 2-(1H-1-imidazolylmethyl) groups are cis to each other.

9. A compound of claim 7 wherein the 3-hydroxy and 2-(1H-1-imidazolylmethyl) groups are trans to each other.

10. A compound of claim 1 which is 2-allyl-6-chloro-2,3-dihydro-3-fluoro-2-(1H-1-imidazolylmethyl) benzo[b]thiophene.

11. A compound of claim 1 which is 2-allyl-3-(2-chloro-6-fluorobenzyloxy)-2,3-dihydro-6-fluoro-2-(1H-1-imidazolylmethylbenzo[b]thiophene.

12. A compound of claim 1 which is 2-allyl-3-(2,6-difluorobenzyloxy)-2,3-dihydro-6-fluoro-2-(1H-1-imidazolylmethylbenzo[b]thiophene.

13. A compound of claim 1 which is 2-allyl-2,3-dihydro-6-chloro-2-(1H-1-imidazolylmethyl)benzo[b]thiophene.

14. A pharmaceutical composition comprising an antifungally effective amount of a compound of claim 1 and a pharmaceutically acceptable carrier or diluent.

15. A composition according to claim 14 suitable for topical administration.

16. A composition according to claim 14 suitable for oral administration.

17. A composition according to claim 14 suitable for parenteral administration.

18. A method of treating susceptible fungal infections which comprises administering to a host in need of such treatment an antifungally effective amount of a compound of claim 1 or a pharmaceutical composition comprising such a compound and a pharmaceutically acceptable carrier or diluent.

19. A method of claim 18 wherein the route of administration is topical.

20. A method of claim 18 wherein the route of administration is oral.

21. A method of claim 18 wherein the route of administration is parenteral.

* * * * *